United States Patent
Leung (10) Patent No.: US 6,376,019 B1
(45) Date of Patent: Apr. 23, 2002

(54) IMPREGNATED APPLICATOR TIP

(75) Inventor: Jeffrey C. Leung, Raleigh, NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 09/951,609

(22) Filed: Sep. 14, 2001

Related U.S. Application Data (62) Division of application No. 09/506,255, filed on Feb. 17, 2000, which is a division of application No. 09/221,997, filed on Dec. 29, 1998, now Pat. No. 6,099,807, which is a division of application No. 08/488,411, filed on Jun. 7, 1995, now Pat. No. 5,928,611.

(51) Int. Cl.$^7$ .................................................. B05D 3/10
(52) U.S. Cl. ......................................................... 427/302
(58) Field of Search ................................. 427/301, 302

(56) References Cited

U.S. PATENT DOCUMENTS

| | | |
|---|---|---|
| 2,439,081 A | 4/1948 | Dickey et al. |
| 2,768,109 A | 10/1956 | Coover, Jr. |
| 2,784,127 A | 3/1957 | Joyner et al. |
| 3,178,379 A | 4/1965 | Wicker, Jr. et al. |
| 3,223,083 A | 12/1965 | Cobey |
| 3,260,637 A | 7/1966 | Bramer |
| 3,468,458 A | 9/1969 | Leigh |
| 3,527,841 A | 9/1970 | Wicker, Jr. et al. |
| 3,559,652 A | 2/1971 | Banitt et al. |
| 3,728,375 A | 4/1973 | Coover, Jr. et al. |
| 3,759,264 A | 9/1973 | Coover, Jr. et al. |
| 3,762,540 A | 10/1973 | Frick et al. |
| 3,770,523 A | 11/1973 | Biswas |
| 3,891,125 A | 6/1975 | Morane et al. |
| 3,964,643 A | 6/1976 | Morane et al. |

(List continued on next page.)

FOREIGN PATENT DOCUMENTS

| | | | |
|---|---|---|---|
| EP | 0 170 526 A2 | | 2/1986 |
| JP | 52-062344 | * | 5/1977 |
| JP | 63-11166 | | 1/1988 |
| JP | U 2-135479 | | 11/1990 |
| WO | 91/09641 | | 7/1991 |
| WO | WO 97/31598 | * | 9/1997 |
| WO | WO 99/10020 | * | 4/1999 |
| WO | WO 99/55394 | * | 11/1999 |

OTHER PUBLICATIONS

J. Fenton, II, et al., "Human Thrombins," *The Journal of Biological Chemistry*, vol. 252, No. 11, pp. 3587–3598 (1977).

M. Carr, Jr., et al., "Influence of $Ca^{2+}$ on the Structure of Reptilase–Derived and Thrombin–Derived Fibrin Gels," *Biochem J.*, vol. 239, pp. 513–516 (1986).

M. Kaminski et al., "Studies on the Mechanism of Thrombin," *The Journal of Biological Chemistry*, vol. 258, No. 17, pp. 10530–10535 (1983).

J. Coombs, "Dictionary of Biotechnology," *Stockton Press* (1986).

R. Linhardt, "Biodegradable Polymers for Controlled Release of Drugs," Controlled Release of Drugs: Polymers and Aggregate Systems, pp. 53–95 (1989).

(List continued on next page.)

*Primary Examiner*—Erma Cameron
(74) *Attorney, Agent, or Firm*—Oliff & Berridge, PLC (57) ABSTRACT

An applicator tip for dispensing a polymerizable and/or cross-linkable material which is porous, absorbent or adsorbent and includes a polymerization or cross-linking initiator. The initiator initiates polymerization or cross-linking when the polymerizable and/or cross-linkable material is dispensed through the applicator tip. The polymerizable and/or cross-linkable material may be applied to a variety of substrates.

13 Claims, 2 Drawing Sheets

U.S. PATENT DOCUMENTS

| | | |
|---|---|---|
| 3,970,505 A | 7/1976 | Hauser et al. |
| 4,042,442 A | 8/1977 | Dombroski et al. |
| 4,291,131 A | 9/1981 | McIntire et al. |
| 4,297,160 A | 10/1981 | Kusayama et al. |
| 4,340,708 A | 7/1982 | Gruber |
| 4,353,463 A | 10/1982 | Seemann |
| 4,364,876 A | 12/1982 | Kimura et al. |
| 4,581,429 A | 4/1986 | Solomon et al. |
| 4,777,230 A | 10/1988 | Kamath |
| 4,801,008 A | 1/1989 | Rich |
| 4,804,691 A | 2/1989 | English et al. |
| 5,059,657 A | 10/1991 | Druliner et al. |
| 5,130,369 A | 7/1992 | Hughes et al. |
| 5,216,096 A | 6/1993 | Hattori et al. |
| 5,219,328 A | 6/1993 | Morse et al. |
| 5,262,200 A | 11/1993 | Puder et al. |
| 5,284,275 A | 2/1994 | Shomer |
| 5,322,912 A | 6/1994 | Georges et al. |
| 5,370,221 A | 12/1994 | Magnusson et al. |
| 5,525,647 A | 6/1996 | Eichmiller |

OTHER PUBLICATIONS

Yin–Chao Tseng et al., "In vivo Evaluation of 2–Cyanoacrylates as Surgical Adhesives," *Journal of Applied Biomaterials*, vol. 1, pp. 111–119 (1990).

F. Leonard, "The n–Alkylalphacyanoacrylate Tissue Adhesives," Annals New York Academy of Sciences, pp. 203–213 1968.

F. Leonard, "Synthesis and Degradation of Poly(alkyl α–Cyanoacrylates)," *Journal of Applied Polymer Science*, vol. 10, pp. 259–272 (1966).

Yin–Chao Tseng et al., "In vitro Toxicity Test of 2–Cyanoacrylate Polymers By Cell Culture Method," *Journal of Biomedical Materials Research*, vol. 24, pp. 1355–1367 (1990).

Loctite Product No. 11067–2 (Rearview Mirror Adhesive); Jan. 1999.

Permatex Product No. ATA–1 (Auto Trim Adhesive); Jan. 1999.

* cited by examiner

IMPREGNATED APPLICATOR TIP

This is a Division of application Ser. No. 09/506,255 filed Feb. 17, 2000; which in turn is a Division of application Ser. No. 09/221,997 filed Dec. 29. 1998 now U.S. Pat. No. 6,099,807, which is a Division of application Ser. No. 08/488,411 filed Jun. 7, 1995, now U.S. Pat. No. 5,928,611. The entire disclosure of the prior applications is hereby incorporated by reference herein in their entirety.

FIELD OF THE INVENTION

This invention relates to the polymerization and/or cross-linking of polymerizable and/or cross-linkable material. This invention also relates to the application of polymerizable and/or cross-linkable material to various substrates with an application device.

BACKGROUND

The terms polymerized and polymerizable, as they are used in the present application, encompass the terms cross-linkable/cross-linked and grafted/graftable as they are defined in the art. For example, not only does the term polymerization include the combination of monomers and prepolymers to form oligomers and polymers, it also includes the attachment of oligomers and polymers by various bridging constituents (cross-linking) and the attachment to oligomers and polymers of side chains having various atomic constituents (grafting).

In some applications, the physical properties of polymerized and/or cross-linked material are extremely important. For example, fast-acting surgical adhesives, sealants, bioactive agent release matrixes and implants utilized in medical, surgical and other in vivo applications require close control of the polymerized and/or cross-linked material. These materials include, for example, alpha-cyanoacrylates disclosed in U.S. Pat. No. 5,328,687 to Leung et al., U.S. Pat. No. 3,527,841 to Wicker et al., U.S. Pat. No. 3,722,599 to Robertson, U.S. Pat. No. 3,995,641 to Kronenthal et al., U.S. Pat. No. 3,940,362 to Overhults and U.S. Pat. application Ser. No. 08/266,647. The subject matter of the foregoing references is incorporated herein by reference.

Typically, when used as adhesives and sealants, cyanoacrylates are applied in monomeric form to the surfaces to be joined or sealed, where typically, in situ anionic polymerization of the monomer occurs, giving rise to the desired adhesive bond with a seal. Implants, such as rods, meshes, screws, and plates, may be formed of cyanoacrylate polymers, formed typically by radical-initiated polymerization.

Efforts to increase the tissue compatibility of alpha-cyanoacrylates have included modifying the alkyl ester group of the cyanoacrylates. For example, increasing the alkyl ester chain link to form the higher cyanoacrylate analogs, e.g., butyl-2-cyanoacrylates and octyl-2-cyanoacrylates, has been found to improve biocompatibility but the higher analogs biodegrade at slower rates than the lower alkyl cyanoacrylates.

Other examples of modified alpha-cyanoacrylates used in biomedical applications include carbalkoxyalkyl, alpha-cyanoacrylates (see, for example, U.S. Pat. No. 3,995,641 to Kronenthal et al.), flurocyanoacrylates (see, for example, U.S. Pat. No. 3,722,599 to Robertson et al.), and alkoxyalkyl 2-cyanoacrylates (see, for example, U.S. Pat. No. 3,559,652 to Banitt et al.). Other efforts have included mixing alpha-cyanoacrylates with dimethyl methylenemalonate and higher esters of 2-cyanoacrylic acid (see, for example, U.S. Pat. No. 3,591,676 to Hawkins et al.).

In other efforts to increase the usefulness of alpha-cyanoacrylate adhesive compositions for surgical applications, certain viscosity modifiers have been used in combination with alkyl alpha-cyanoacrylate monomers, such as methyl alpha-cyanoacrylate. See, for example, U.S. Pat. No. 3,564,078 (wherein the viscosity modifier is poly (ethyl 2-cyanoacrylate)) and U.S. Pat. No. 3,527,841 (wherein the viscosity modifier is poly(lactic acid)).

In U.S. Pat. No. 5,328,687 to Leung et al., the entire contents of which are hereby incorporated by reference, the use of formaldehyde scavengers has been proposed to improve biocompatibility of the alpha-cyanoacrylate polymers, whose biodegradation produces formaldehyde, for use in in vivo applications. Additionally, in U.S. application Ser. No. 08/266,647, the entire contents of which are incorporated herein by reference, the biodegradation rate of alpha-cyanoacrylate polymer is accomplished by regulating the pH of an immediate in vivo environment of a biocompatible composition. It is also known that various compounds can affect polymerization of alpha-cyanoacrylate monomers, including acids to inhibit or slow polymerization (e.g., U.S. Pat. No. 3,896,077 to Leonard et al.), and bases to accelerate polymerization (e.g., U.S. Pat. No. 3,759,264 to Coover and U.S. Pat. No. 4,042,442 to Dombroski et al.).

Likewise, many polymerization and/or cross-linking inhibitors are conventionally added to polymerizable and/or cross-linkable materials in order to increase their shelf life. However, the amount of polymerization inhibitor that may be added to the polymerizable and/or cross-linkable material is limited due to the negative impact on any subsequent polymerization process. In particular, a large quantity or concentration of polymerization inhibitor that is added to stabilize polymerizable and/or cross-linkable material may stabilize the polymerizable and/or cross-linkable material to an extent that will adversely affect polymerization. Accordingly, conventional polymerizable and/or cross-linkable materials may contain only a limited amount of polymerization inhibitor.

For certain applications of polymerizable and/or cross-linkable material there exists a need for controlling the setting time of polymerizable and/or cross-linkable material. For example, surgical adhesives used for some surgical procedures require rapidly or relatively less rapidly setting polymerization materials, depending on the procedure involved (e.g., U.S. Pat. No. 5,328,687 to Leung et al. and U.S. application Ser. No. 08/266,647, the disclosures of which are incorporated herein by reference). Other bonding processes, including sealing and bonding processes in the construction and automotive industries, molding processes in the plastic industry, and coating processes in the textile and electronics industries, require a variety of setting times. Many of these applications require control of the setting time in order to facilitate adequate strength, elasticity and hardness of a polymerized material while also providing the necessary amount of working time to apply the polymerized material to a desired substrate.

Various dispensing devices have been developed for the purposes of applying and mixing multiple components simultaneously. For example, U.S. Pat. No. 3,468,548 to Leigh discloses a dispenser for dispensing two paste-like materials, such as creams or gels. One of the materials is stored in a tube and a second material is stored in a chamber of a nozzle attached to the tube. When the first material is forced from the tube, it flows through the nozzle and mixes with the second material.

U.S. Pat. No. 3,891,125 to Morane et al. describes a device for storing two products separately and mixing the products prior to application. One product is stored in a nozzle attached to a container containing a second product. The product in the nozzle drops by the force of gravity into the container containing the second product and mixing occurs. subsequently, the mixed products may be forced from the container and applied to a suitable substrate.

U.S. Pat. No. 3,770,523 to Biswas relates the application of a thickened slurry explosive into a bore hole or a container. A stream of slurry explosive is thickened by admixing the stream with a cross-linking agent by plurality of jet streams impinging on the slurry stream.

U.S. Pat. No. 4,801,008 to Rich discloses a disposable cartridge including a chamber containing a plurality of inter-reacting components of an adhesive system. The components are separated from each other by a barrier film. They are expelled through a nozzle where they are mixed with a static mixing element.

SUMMARY OF THE INVENTION

The need continues to exist in the polymer and resin and coating industries for improved processes for controlling the properties of polymerized materials by controlling the polymerization and/or cross-linking rate and/or extent. Moreover, there is a need to provide a simplified and economical process for applying polymerizable and/or cross-linkable materials to various substrates. We have invented an inexpensive device and method that simplify the application of a variety of polymerizable and/or cross-linkable materials to substrates while providing control over the properties of the material, especially fast-curing materials and medicinal use materials.

This invention provides a system for dispensing a polymerizable and/or cross-linkable material from an applicator, comprising an applicator tip with a polymerization and/or cross-linking initiator for the material. The applicator tip according to the present invention provides several advantages, including the ability to:

a) control the molecular weight of the polymerized or cross-linked material;

b) control the setting time of the polymerized or cross-linked material;

c) provide precision and convenience in applying the material to a substrate;

d) extend the material shelf life;

e) reduce the presence of residual monomer and avoid associated monomer odors; and f) control the flow properties of applied materials.

The applicator tip of the present invention may be used to apply to various substrates a wide variety of monomers and polymers that undergo polymerization and/or cross-linking by utilization of a polymerization or cross-linking initiator. Moreover, the applicator tip of the present invention may be utilized in a wide variety of monomer and polymer systems, such as, for example, in the application of plural component adhesive systems.

DETAILED DESCRIPTION OF PREFERRED EMBODIMENTS

The applicator tip of the present invention may be employed in a variety of processes for the application of a variety of polymerizable and/or cross-linkable materials. In particular, the polymerizable and/or cross-linkable materials include inorganic and organic materials and combinations thereof.

Suitable inorganic materials include but are not limited to siloxanes, silicones, polysulfides and polyphosphazenes. Suitable organic polymerizable and/or cross-linkable materials include but are not limited to natural, synthetic, and semi-synthetic materials. Suitable natural polymerizable and/or cross-linkable materials include but are not limited to polysaccharides, such as starch, cellulose, pectin, seaweed gums or vegetable gums; polypeptides or proteins, such as casein, albumin, globulin, or carotin; or hydrocarbons, such as rubber and polyisoprene.

Suitable organic synthetic materials include but are not limited to thermoplastics and thermoplastic elastomers, such as nylon and other polyamides, polyvinylchloride, polycarbonates, polyethylene, polystyrene, polypropylene, fluorocarbon resins, polyurethane and acrylate resins; or thermosetting elastomers, such as phenolics, urethanes, epoxies, alkyds or polyesters. Suitable organic semi-synthetic materials include but are not limited to celluloses, such as rayon, methylcellulose, or cellulose acetate; or modified starches, such as starch acetate, and the like. Examples of suitable polymerizable and/or cross-linkable materials include but are not limited to those set forth in U.S. Pat. No. 5,328,687 to Leung et al., U.S. Pat. No. 3,728,375 to Coover, Jr., et al., U.S. Pat. No. 3,970,505 to Hauser et al., U.S. Pat. No. 4,297,160 to Kusayama et al., U.S. Pat. No. 4,340,708 to Gruber, U.S. Pat. No. 4,777,230 to Kamath, U.S. Pat. No. 5,130,369 to Hughes et al. and U.S. application Ser. No. 08/226,647, the entire disclosures of which are incorporated herein by reference. The polymerizable and/or cross-linkable material may include one of the above-mentioned materials or may contain one or more of the materials in a mixture. The material may also be composed of monomers, polymers, or oligomers of the above-mentioned polymerizable and/or cross-linkable materials.

For example, suitable polymerizable and/or cross-linkable materials include 1,1-disubstituted ethylene monomers. Useful 1,1-disubstituted ethylene monomers include, but are not limited to, monomers of the formula:

$$CHR=CXY \qquad (I)$$

wherein X and Y are each strong electron withdrawing groups, and R is H, —CH=CH$_2$ or, provided that X and Y are both cyano groups, a C$_1$–C$_4$ alkyl group.

Examples of monomers within the scope of formula (I) include alpha-cyanoacrylates, vinylidene cyanides, C$_1$–C$_4$ alkyl homologues of vinylidene cyanides, dialkyl 2-methylene malonates, acylacrylonitriles, vinyl sulfinates and vinyl sulfonates of the formula CH$_2$=CX'Y' wherein X' is —SO$_2$R' or —SO$_3$R' and Y' is —CN, —COOR', —COCH$_3$, —SO$_2$R' or —SO$_3$R', and R' is H or hydrocarbyl.

Preferred monomers of formula (I) for use in this invention are alpha-cyanoacrylates. These monomers are known in the art and have the formula wherein $R^2$ is hydrogen and $R^3$ is a hydrocarbyl or substituted hydrocarbyl group; a group having the formula —$R^4$—O—$R^5$—O—$R^6$, wherein $R^4$ is a 1,2—alkylene group having 2–4 carbon atoms, $R^5$ is an alkylene group having 2–4 carbon atoms, and $R^6$ is an alkyl group having 1–6 carbon atoms; or a group having the formula wherein and $R^8$ is an organic moiety.

Examples of suitable hydrocarbyl and substituted hydrocarbyl groups include straight chain or branched chain alkyl groups having 1–16 carbon atoms; straight chain or branched chain $C_1$–$C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

In the cyanoacrylate monomer of formula (II), $R^3$ is preferably an alkyl group having 1–10 carbon atoms or a group having the formula —$AOR^9$, wherein A is a divalent straight or branched chain alkylene or oxyalkylene radical having 2–8 carbon atoms, and $R^9$ is a straight or branched alkyl radical having 1–8 carbon atoms.

Examples of groups represented by the formula —$AOR^9$ include 1-methoxy-2-propyl, 2-butoxyethyl, 2-isopropoxethyl, 2-methoxyethyl, 2-ethoxyethyl and 3-methoxybutyl.

Especially advantageous alpha-cyanoacrylate monomers for use in this invention are methyl alpha-cyanoacrylate, butyl alpha-cyanoacrylate, 2-octyl alpha-cyanoacrylate, 1-methoxy-2-propyl cyanoacrylate, 2-butoxyethyl cyanoacrylate, 2-isopropoxyethyl cyanoacrylate and 3-methoxybutyl cyanoacrylate. Equally advantageous are 2-methylene malonates, such as dimethyl 2-methylenemalonate.

The alpha-cyanoacrylates of formula (II) wherein $R^3$ is a hydrocarbyl or substituted hydrocarbyl group can be prepared according to methods known in the art. Reference is made, for example, to U.S. Pat. Nos. 2,721,858 and 3,254,111, each of which is hereby incorporated by reference herein. For example, the alpha-cyanoacrylates can be prepared by reacting an alkyl cyanoacetate with formaldehyde in a non-aqueous organic solvent and in the presence of a basic catalyst, followed by pyrolysis of the anhydrous intermediate polymer in the presence of a polymerization inhibitor. The alpha-cyanoacrylate monomers prepared with low moisture content and essentially free of impurities are preferred for biomedical use.

The alpha-cyanoacrylates of formula (II) wherein $R^3$ is a group having the formula —$R^4$—O—$R^5$—O—$R^6$ can be prepared according to the method disclosed in U.S. Pat. No. 4,364,876 (Kimura et al.), which is hereby incorporated by reference herein. In the Kimura et al. method, the alpha-cyanoacrylates are prepared by producing a cyanoacetate by esterifying cyanoacetic acid with an alcohol or by transesterifying an alkyl cyanoacetate and an alcohol; condensing the cyanoacetate and formaldehyde or paraformaldehyde in the presence of a catalyst at a molar ratio of 0.5–1.5:1, preferably 0.8–1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate The alpha-cyanoacrylates of formula (II) wherein $R^3$ is a group having the formula can be prepared according to the procedure described in U.S. Pat. No. 3,995,641 to Kronenthal et al., which is hereby incorporated by reference. In the Kronenthal et al. method, such alpha-cyanoacrylate monomers are prepared by reacting an alkyl ester of an alpha-cyanoacrylic acid with a cyclic 1,3-diene to form a Diels-Alder adduct which is then subjected to alkaline hydrolysis followed by acidification to form the corresponding alpha-cyanoacrylic acid adduct. The alpha-cyanoacrylic acid adduct is preferably esterified by an alkyl bromoacetate to yield the corresponding carbalkoxymethyl alpha-cyanoacrylate adduct. Alternatively, the alpha-cyanoacrylic acid adduct may be converted to the alpha-cyanoacrylyl halide adduct by reaction with thionyl chloride. The alpha-cyanoacrylyl halide adduct is then reacted with an alkyl hydroxyacetate or a methyl substituted alkyl hydroxyacetate to yield the corresponding carbalkoxymethyl alpha-cyanoacrylate adduct or carbalkoxy alkyl alpha-cyanoacrylate adduct, respectively. The cyclic 1,3-diene blocking group is finally removed and the carbalkoxy methyl alpha-cyanoacrylate adduct or the carbalkoxy alkyl alpha-cyanoacrylate adduct is converted into the corresponding carbalkoxy alkyl alpha-cyanoacrylate by heating the adduct in the presence of a slight deficit of maleic anhydride.

Examples of monomers of formula (II) include cyanopentadienoates and alpha-cyanoacrylates of the formula:

wherein Z is —CH=$CH_2$ and $R^3$ is as defined above. The monomers of formula (III) wherein $R^3$ is an alkyl group of 1–10 carbon atoms, i.e., the 2-cyanopenta-2,4-dienoic acid esters, can be prepared by reacting an appropriate 2-cyanoacetate with acrolein in the presence of a catalyst such as zinc chloride. This method of preparing 2-cyanopenta-2,4-dienoic acid esters is disclosed, for example, in U.S. Pat. No. 3,554,990, which is incorporated by reference herein.

The polymerizable and/or cross-linkable materials may include additives, such as polymerization inhibitors or stabilizers, viscosity modifiers, free radical scavengers, pH modifiers (e.g., U.S. application Ser. No. 08/266,647, the subject matter of which is incorporated herein by reference), other monomers, formaldehyde scavengers (e.g., U.S. Pat. No. 5,328,687 to Leung et al., the subject matter of which is incorporated herein by reference), colorants, lubricants, release or transfer agents, surfactants, defoamants, plasticizers, mixtures thereof and other additives.

The polymerizable and/or cross-linkable material may be neat (no additional compounds added) or in a solvent, emulsion or suspension. Suitable solvents according to the present invention include alcohol, ether alcohol, hydrocarbons, halogenated hydrocarbons, ethers, acetals, ketones, esters, acids, sulfur- or nitrogen-containing organic compounds, mixtures thereof and the like. Other suitable solvents are disclosed in U.S. Pat. No. 5,130,369 to Hughes et al. and U.S. Pat. No. 5,216,096 to Hattori et al., the entire disclosures of which are incorporated herein by reference. These solvents may be used either independently or in combination of two or more. They may also be used in conjunction with water to the extent that the polymerizable and/or cross-linkable material is dissolved or suspended in such a mixture. The total amount of solvent that may be incorporated into the polymerizable and/or cross-linkable material may be 0 to 99, preferably 1 to 50, and more preferably 3 to 25 percent by weight. Selection of the amount will, of course, depend on the desired monomer and process conditions, and amounts outside these ranges may be acceptable.

The polymerizable and/or cross-linkable material may also contain polymerization initiators or inhibitors, chain transfer agents, stabilizers, or mixtures thereof. Suitable polymerization inhibitors and stabilizers are disclosed in U.S. Pat. No. 5,322,912 to Georges et al., U.S. Pat. No. 4,581,429 to Solomon et al., U.S. Pat. No. 4,340,708 to Gruber, U.S. Pat. No. 4,364,876 to Kimura et al. and U.S. Pat. No. 4,297,160 to Kusayama et al. The entire disclosures of these patents are incorporated herein by reference. The stabilizer or inhibitor may be added to the polymerizable and/or cross-linkable material in an amount of 0 to 50, preferably 0.001 to 25, and more preferably 0.002 to 10 percent by weight. Selection of the amount will, of course, depend on the desired monomer and process conditions, and amounts outside these ranges may be acceptable.

Suitable chain transfer agents which may be incorporated into the polymerizable and/or cross-linkable material of the present invention include those disclosed in U.S. Pat. No. 5,130,369 to Hughes et al., the entire disclosure of which is incorporated herein by reference.

The amount of chain transfer agent included in the polymerizable and/or cross-linkable material may be 0 to 25, preferably 1 to 15, and more preferably 2 to 10 percent by weight. Selection of the amount will, of course, depend on the desired monomer and process conditions, and amounts outside these ranges may be acceptable.

Suitable viscosity modifiers, plasticizers and lubricants, which may or may not themselves be polymerizable and/or cross-linkable, that may be added to the polymerizable and/or cross-linkable material of the subject invention include those set forth in U.S. Pat. No. 4,297,160 to Kusayama et al., the entire disclosure of which is incorporated herein by reference. The polymerizable and/or cross-linkable material according to the present invention may also contain formaldehyde scavengers and pH modifiers as disclosed in U.S. Pat. No. 5,328,687 to Leung et al. and U.S. application Ser. No. 08/266,647, respectively, the disclosures of which are totally incorporated herein by reference.

Figure 1:
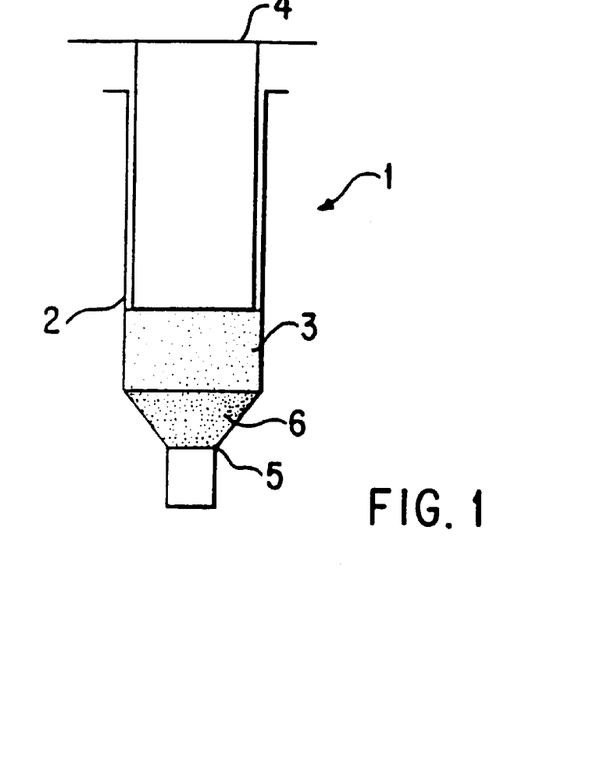
FIG. 1 is a side elevational view of an applicator device in accordance with this invention for application of a polymerizable and/or cross-linkable material.

Referring now in greater detail to the figures of the drawings, an applicator device embodying one aspect of the present invention is generally shown at 1 in FIG. 1.

The device comprises a cylindrical applicator container 2 holding a polymerizable and/or cross-linkable material 3, a plunger 4 for forcing the material 3 from the container 2 and an applicator tip 5 having a portion 6 thereof comprising a polymerization and/or cross-linking initiator.

Figure 2:
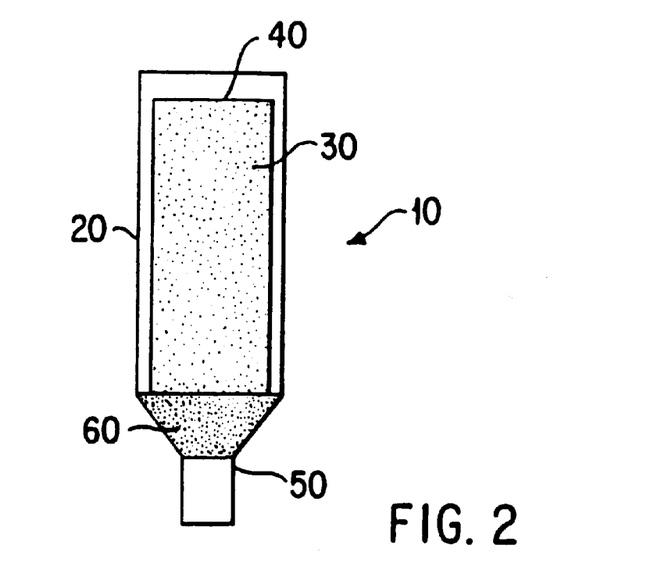
FIG. 2 is a side elevational view of an alternative applicator device according to the invention.

FIG. 2 illustrates another embodiment of the invention and includes an applicator device 10. The device comprises a cylindrical applicator container 20 holding a polymerizable and/or cross-linkable material 30 enclosed in a frangible vial 40, and an applicator tip 50 having a portion 60 thereof comprising a polymerization and/or cross-linking initiator.

Figure 3:
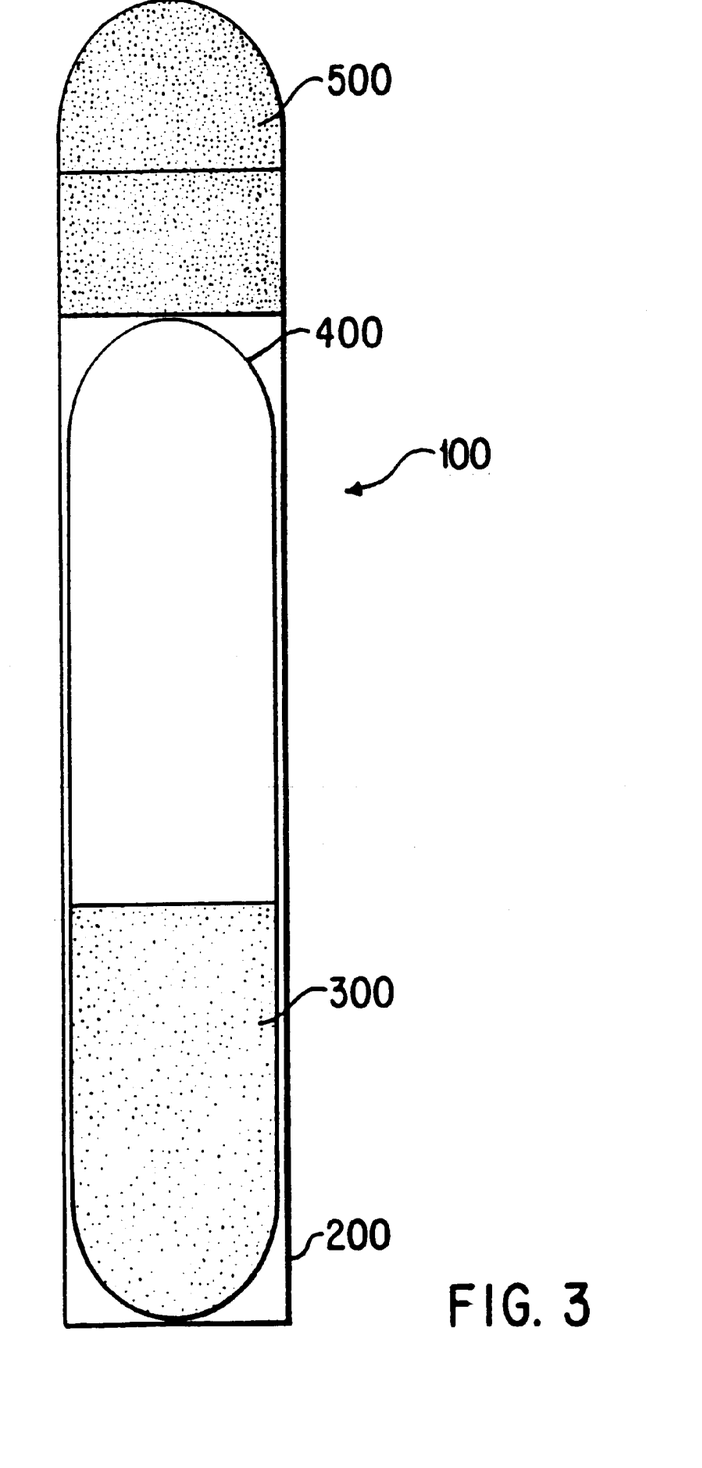
FIG. 3 is a side elevational view of an alternative applicator device according to the invention.

FIG. 3 illustrates another embodiment, and includes an applicator device 100. The device comprises a cylindrical applicator container 200 holding polymerizable and/or cross-linkable material 300 enclosed in a frangible vial 400, and an applicator tip 500 containing a polymerization and/or cross-linking initiator.

The applicator tip according to the present invention may have a variety of suitable shapes, including but not limited to conical, cylindrical, chisel or polygonal shapes. For example, the tip may be a tube, cannula, catheter, single or multi-lumen shape, or comprise a rolling ball, brush, cotton swab or similar tip. Preferably the applicator tip is conical. The end having decreased circumference is preferably the end from which the material exits from the applicator tip and is fashioned in a manner to facilitate application of the material to any suitable substrate. The length of the applicator tip may also be varied depending on various application parameters, such as the proximity of the applicator container holding the polymerizable and/or cross-linkable material to the substrate to which the material is to be applied. The size of the tip end in which the material exits the tip may be varied depending on the application.

The applicator container according to the present invention may also be in a variety of shapes and sizes depending on the intended use. For example, for application of limited amounts of polymerizable and/or cross-linkable material, the applicator container may be a syringe, a tube, a vial, a bulb or a pipette. For example, a frangible closed tube 400 of polymerizable and/or cross-linkable material 300 in a flexible container 200 as shown in FIG. 3 is a preferred type of applicator. For applications of the polymerizable and/or cross-linkable material in greater amounts, applicator containers such as, for example, tanks or reactor vessels may be utilized.

The applicator tip according to the present invention may be detachable from the applicator container holding the polymerizable and/or cross-linkable material. Such an applicator tip could be attached to the applicator container prior to use and detached from the applicator container subsequent to use in order to prevent premature polymerization or cross-linking of the unapplied material in the applicator container. At this point the applicator At tip may be discarded and a new applicator tip may be attached to the applicator container for subsequent use or the applicator tip may be reused.

Additionally, the applicator tip according to the present invention may comprise multiple parts, with at least one part comprising the initiator. For example, the component comprising the initiator may be fabricated separately from the other component(s) of the applicator tip and assembled prior to attachment to the applicator container.

The applicator tip may also be in the form of a nozzle for atomizing liquid polymerizable and/or cross-linkable linkable materials. Conical, flat spray or condensed stream nozzles are suitable.

The applicator tip according to the present invention may be utilized in manual or automated applications. For example, manual methods of application may include utilization of hand-held devices such as syringes, adhesive guns, pipettes, eyedroppers and the like. Automated application processes include injection molding and robotic painting/sealing/adhering.

The applicator tip and the applicator container may also be an integral unit. The unit may be preformed as a single piece and charged with polymerizable and/or cross-linkable material. After application of material from the applicator container, the unit may be discarded. Additionally, such an integral applicator tip/applicator container unit may be fashioned to provide the capability of recharging the unit with new material as a multiple use device.

The applicator tip may be composed of any of a variety of materials including polymerized materials such as plastics, foams, rubber, thermosets, films or membranes. Additionally, the applicator tip may be composed of materials such as metal, glass, paper, ceramics, cardboard and the like. The applicator tip material may be porous, absorbent or adsorbent in nature to enhance and facilitate loading of the initiator on or within the applicator tip. For example, the applicator tip may be composed of a material having random pores, a honey-comb material, a material having a woven pattern, etc. The degree of porosity will depend on the materials being used.

The applicator tip according to the present invention, where it connects to the applicator container, may have an elongated tubular portion, out of which the mixed polymerizing and/or cross-linking material is expelled. A portion of the applicator tip which is immediately downstream of the applicator container is advantageously porous in order to avoid a sharp pressure drop and ensure a constant mixed ratio profile. The structure can preferably trap any barriers or materials used to separate multiple components within the applicator container. Thus, any such barriers will not clog the device.

The initiators that initiate polymerization and/or cross-linking of the material may be applied to a surface portion or to the entire surface of the applicator tip, including the interior and the exterior of the tip. Alternatively, the initiator may be coated only on an internal surface of the applicator tip. Preferably, only a portion of the interior of the applicator tip is coated with the initiator.

The initiator on the applicator tip may be in the form of a solid, such as a powder or a solid film, or in the form of a liquid, such as a viscous or paste-like material. The initiator may also include a variety of additives, such as surfactants or emulsifiers. Preferably, the initiator is soluble in the polymerizable and/or cross-linkable material, and/or comprises or is accompanied by at least one surfactant which, in embodiments, helps the initiator co-elute with the polymerizable and/or cross-linkable material. In embodiments, the surfactant may help solubilize the initiator in the polymerizable and/or cross-linkable material.

Particular initiators for particular systems may be readily selected by one of ordinary skill in the art without undue experimentation. Suitable initiators include, but are not limited to, detergent compositions; surfactants: e.g., nonionic surfactants such as polysorbate 20 (e.g., Tween 20™), polysorbate 80 (e.g., Tween 80™) and polymers, cationic surfactants such as tetrabutylammonium bromide, anionic surfactants such as sodium tetradecyl sulfate, and amphoteric or zwitterionic surfactants such as dodecyldimethyl(3-sulfopropyl)ammonium hydroxide, inner salt; amines, imines and amides, such as imidazole, tryptamine, urea, arginine and povidine;

phosphines, phosphites and phosphonium salts, such as triphenylphosphine and triethyl phosphite; alcohols such as ethylene glycol, methyl gallate, ascorbic acid, tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat 336; organometallics such as cobalt naphthenate and manganese acetylacetonate; and radical initiators and radicals, such as di-t-butyl peroxide and azobisisobutyronitrile. The polymerizable and/or cross-linkable material may also contain an initiator which is inactive until activated by a catalyst or accelerator (included within the scope of the term "initiator" as used herein) in the applicator tip. For example, monomer containing benzoyl peroxide may be used as a polymerizable material in association with a tip containing an amine accelerator, or monomer containing methyl ethyl ketone peroxide may be used as a polymerizable material in association with a tip containing cobalt naphthenate. Initiators activated by stimulation such as heat and/or light (e.g., ultraviolet or visible light) are also suitable if the tip and/or applicator is appropriately subjected to such stimulation.

The initiator may be applied to the surface of the applicator tip or may be impregnated or incorporated into the matrix or internal portions of the applicator tip. For example, the initiator may be applied to the applicator tip by spraying, dipping, or brushing the applicator tip with a liquid medium containing the initiator. The liquid medium may include non-aqueous solvents, such as ether, acetone, ethanol, pentane or mixtures thereof; or may include aqueous solutions. Preferably, the liquid medium is a low boiling point solvent.

Additionally, the initiator on the applicator tip may be present in a variety of concentrations in the medium ranging from 0 to 50%, preferably from 0.001 to 25%, and most preferably from 0.01 to 10% by wt.

Selection of the amount will, of course, depend on the desired monomer and process conditions, and amounts outside these ranges may be acceptable.

The initiator may be applied to the applicator tio in the form of a preformed film of initiator. The initiator may be applied as a solid by vapor deposition such as by sputtering. Additionally, the initiator may be incorporated into the applicator tip, for example, during the fabrication of the tip. This can be accomplished by mixing the initiator with the applicator tip material prior to molding the applicator tip material into the desired form.

Subsequent to application of the initiator on or in the applicator tip, the applicator tip may be dried or heated to evaporate or volatilize the liquid medium or to evenly distribute or impregnate initiator in the applicator tip. This can be accomplished by drying the applicator tip at room temperature or by heating the applicator tip in a conventional device such as a conventional oven, vacuum oven, microwave oven, or UV/visible light.

Additionally, the container holding the polymerizable and/or cross-linkable material may comprise the initiator. For example, the polymerizable and/or cross-linkable material may be stored separately within the applicator container so as not to contact the initiator within the container. The applicator container may be lined or coated with the initiator or the initiator may be stored in a compartment separate from the polymerizable and/or cross-linkable material within the applicator container. For example, in the device of FIG. 3, the initiator may be coated on the internal surface of body 200.

Within the applicator tip, static or dynamic mixers may be provided to ensure thorough mixing of the polymerizable and/or cross-linkable material with the initiator. Preferable static mixers include internal tortuous paths.

The applicator tip according to the present invention may also be utilized in conjunction with multi-component polymerizable and/or cross-linkable material systems having materials that must remain physically separated from each other prior to application in order to avoid chemical reactions therebetween. Such multi-component cartridges, for instance, are disclosed in U.S. Pat. No. 3,915,297 to Rausch, U.S. Pat. Nos. 4,493,436, 4,538,920 and 4,801,008 to Rich, the entire disclosures of which are incorporated herein by reference.

Pressure may be applied to the polymerizable and/or cross-linkable material to force the material from the applicator container through the applicator tip. As the polymerizable and/or cross-linkable material passes through the applicator tip, the material contacts the initiator, thereby initiating polymerization and/or cross-linking of the material. The shape of the applicator tip preferably enhances mixing of the material and the initiator to provide a homogeneous mixture. The shape of the applicator tip also facilitates application of the polymerizing and/or cross-linking material to a suitable substrate. The initiator may co-elute with the polymerizable and/or cross-linkable material, or may remain in the tip.

The material according to the present invention may be applied to a variety of substrates for the purposes of protecting, sealing, and bonding surfaces together. Suitable substrates include metals, plastics, rubbers, wood, ceramics, fabrics, cement, paper, living tissue and the like. For example, the polymerizable and/or cross-linkable material may be useful as tissue adhesives, sealants for preventing bleeding or for covering open wounds, systems for delivery of therapeutic or other bioactive agents, and other biomedical applications. They find uses in, for example, closing surgically incised or traumatically lacerated tissues; setting fractured bone structures; retarding blood flow from wounds; aiding repair and regrowth of living tissues; providing implantable matrixes for delivering bioactive agents; and providing structural implants.

The applicator tip according to the present invention provides control over the molecular weight of the polymerized or cross-linked material. For example, the amount of initiator applied to the applicator tip may be increased to an extent that would provide more complete polymerization of a polymerizable and/or cross-linkable material over conventional methods that incorporate the polymerization initiator in the polymerizable and/or cross-linkable material before application thereof.

The applicator tip according to the present invention also provides control over the setting time of the material. For example, the amount of initiator applied to the applicator tip may be varied from one tip to another in order to provide control over the length of working time for application of a material. Additionally, applicator tips having different amounts or types of initiators may be interchanged to provide different setting times during application of a particular material or different materials.

The applicator tip according to the present invention also provides extended shelf life of the polymerizable and/or cross-linkable material. For example, by providing an increased amount of polymerization initiator on the applicator tip, the polymerizable and/or cross-linkable material may be provided with a greater amount of polymerization inhibitors or stabilizers that would decrease premature polymerization.

The applicator tip according to the present invention also provides increased ease of application of the polymerizable and/or cross-linkable material by providing improved rheological properties of this material during application to a substrate. For example, surfactants incorporated into the polymerization initiator on the applicator tip can provide the polymerizing material exiting the applicator tip with enhanced fluidity, and can assist the initiator to co-elute with the material.

The following examples illustrate specific embodiments of the present invention. One skilled in the art will recognize that the appropriate reaction parameters, reagents, component ratios/concentrations and device dimensions may be adjusted as necessary to achieve specific polymerized product characteristics. All parts and percentages are by weight unless otherwise indicated.

EXAMPLES

Initiators in several weight percentages are mixed with acetone and stirred for at least 30 minutes to achieve homogeneity. Porous plastic tips of applicators as shown in FIG. 3 are soaked in the initiator solution for several minutes, removed from the solution, and attached to the open end of flexible butyrate tubes containing glass-ampulized monomer material as shown in FIG. 3. (The butyrate tubes soften upon contact with the acetone, thus "welding" the tip to the applicator body.) The applicators are allowed to dry overnight in a fume hood. A control tip with no initiator is prepared using pure acetone solvent.

In an upright position, the applicator tubes are squeezed to shatter the glass ampules, thereby releasing monomer material. The applicators are then inverted, and the monomer material is forced out of the tip by squeezing the applicator tube. As the material comes out of the tubes, a thin line of the material is run along the back of a person's hand (2–3 inches), and the time for complete polymerization is recorded. The results are shown in Table 1, and demonstrate the effectiveness of the claimed invention in controlling polymerization time.

TABLE 1

| Polymerizable Material | Initiator (wt. %) | Setting Time (seconds) |
| --- | --- | --- |
| 2-octyl cyanoacrylate | none | >240 |
| 2-octyl cyanoacrylate | 0.01% Tween 20 | 45 |
| 2-octyl cyanoacrylate | 0.05% Tween 20 | 30 |
| 2-octyl cyanoacrylate | 0.15% Tween 20 | 20 |
| 2-isopropoxyethyl cyanoacrylate | none | >240 |
| 2-isopropoxyethyl cyanoacrylate | 2.5% Tween 20 | 50 |
| 2-isopropoxyethyl cyanoacrylate | 5.0% Tween 20 | <40 |
| dimethyl 2-methylenemalonate | none | >150 |
| dimethyl 2-methylenemalonate | 2.5% tetrabutyl-ammonium bromide | 50 |

What is claimed is:

1. A method of preparing an applicator tip for dispensing a polymerizable or cross-linkable monomer material, comprising:

applying to at least a portion of an applicator tip a polymerization or cross-linking accelerator or initiator for said monomer material, wherein said accelerator or initiator is applied to said tip by mixing said accelerator or initiator with material used to form said tip prior to forming said tip.

2. A method according to claim 1, wherein said monomer material is an adhesive monomer material.

3. A method according to claim 1, wherein said monomer material comprises 1,1-disubstituted ethylene monomers.

4. A method according to claim 1, wherein said monomer material comprises monomers selected from the group consisting of butyl and octyl α-cyanoacrylates.

5. A method according to claim 1, wherein a shape of said applicator tip is selected from the group consisting of conical, cylindrical, chisel and polygonal shapes.

6. A method according to claim 5, wherein said applicator tip has a conical shape.

7. A method according to claim 5, wherein said applicator tip has a chisel shape.

8. A method according to claim 5, wherein said applicator tip has a polygonal shape.

9. A method according to claim 1, wherein said applicator tip comprises a polymerized material.

10. A method according to claim 1, wherein said applicator tip comprises a material selected from the group consisting of metal, glass, paper, ceramics, and cardboard.

11. A method according to claim 1, wherein said applicator tip comprises a plastics material.

12. A method according to claim 1, wherein said applicator tip is at least one of porous, absorbent and adsorbent in nature.

13. A method according to claim 1, wherein said applicator tip is a porous applicator tip.

* * * * *